United States Patent [19]
Götz et al.

[11] Patent Number: 4,925,942
[45] Date of Patent: May 15, 1990

[54] PREPARATION OF QUINUCLIDINE-3-METHANOL

[75] Inventors: Josef Götz, Heidelberg; Winfried Orth, Hassloch; Wolfgang Weiss, Neckarhausen; Bernd Rapp, Ketsch; Hans W. Kleffner, Battenberg, all of Fed. Rep. of Germany

[73] Assignee: Rutgerswerke AG, Fed. Rep. of Germany

[21] Appl. No.: 384,987

[22] Filed: Jul. 24, 1989

[30] Foreign Application Priority Data

Aug. 10, 1988 [DE] Fed. Rep. of Germany ....... 3827117

[51] Int. Cl.$^5$ ........................................... C07D 453/02
[52] U.S. Cl. .................................................... 546/133
[58] Field of Search ........................................ 546/133

[56] References Cited

U.S. PATENT DOCUMENTS 4,546,185 10/1985 Bondiou et al. .................... 546/133

Primary Examiner—Mary C. Lee
Assistant Examiner—Robert C. Whittenbaugh
Attorney, Agent, or Firm—Bierman & Muserlian

[57] ABSTRACT

A process for the preparation of quinuclidine-3-methanol comprising reacting quinuclidine-3-one acid addition salt with an alkali metal cyanide in an aqueous media to obtain 3-cyano-3-hydroxy-quinuclidine, reacting the latter with anhydrous methanol in the presence of hydrogen chloride gas followed by treatment with aqueous alkali to obtain methyl 3-hydroxy-quinuclidine-3-carboxylate, reacting the latter with thionyl chloride to form methyl 1-azabicyclo(2,2,2)oct-2-ene-3-carboxylate, hydrogenating the latter with Raney nickel to obtain methyl 1-azabicyclo(2,2,2)octane-3-carboxylate and reducing the latter to obtain quinuclidine-3-methanol which is an intermediate for mequitazine which is useful as an antihistaminic.

1 Claim, No Drawings

PREPARATION OF QUINUCLIDINE-3-METHANOL

STATE OF THE ART

Two synthesis methods starting with quinuclidine-3-one are known in the literature. EP-A 0102283 describes subjecting quinuclidine-3-one to a Wittig reaction to form quinclidine-3-methene which is reacted with lithium alanate and titainium (IV) compounds to form a complex which is dissociated wiyh hydrogen peroxide with formation of quinuclidine-3-methanol Although the yield of 45% is relatively satisfactory, the process is undesirable since the individual raction steps must be carried out under protective gas and involve a safety risk or respectively an increased investment cost. The needed auxiliary chemicals, particularly methylene triphenyl phosphorane, are expensive and make the process unprofitable and also involve disposal problems.

According to Grob. Helv. Chim. Acta, Vol. 37 (1954), p. 1689, cyanide is reacted with quinuclidine-3-one and the respective cyanohydrin is hydrolyzed to acid, and the latter is esterified and the hydroxy ester is dehydrated, hydrogenated, and reduced to quinuclidine-3-methanol. Although the individual steps of this reaction sequence are all relatively simple, the total yield overall is as low as 4.9% which means the process is not commerical feasible.

OBJECTS OF THE INVENTION

It is an object of the invention to provide an economical, exvironmentally safe process for the preparation of quinuclidine-3-one in good yields.

This and other objects and advantages of the invention will become obvious from the following detailed description.

THE INVENTION

The novel process of the invention for the preparation of quinuclidine-3-methanol comprises reacting quinuclidine-3-one acid addition salt with an alkali metal cyanide in an aqueous meda to obtain 3-cyano-3-hydroxy-quinuclidine, reacting the latter with anhydrous methanol in the presence of hydrogen chloride gas followed by treatment with aqueous alkali to obtain methyl 3-hydroxy-quinuclidine-3-carboxylate, reacting the latter with thionyl chloride to form methyl 1-azabicyclo(2,2,2)oct-2-ene-3-carboxylate, hydrogenating the latter with Raney nickel to obtain methyl 1-azabicyclo(2,2,2)octane-3-carboxylate and reducing the latter to obtain quinuclidine-3-methanol.

The process of the invention has the advantage that quinuclidine-3-methanol is produced with excellent purity with an overall yield of more than 30% based on the quinuclidine-3-one. The improved results are due to (a) the imide ester step wherein methyl quinuclidine-3-carboxylate is reacted to form methyl 3-hydroxy-quinuclidine-3-carboxylate, (b) dehydration with thionyl chloride and (c) hydrogenation of methyl quinuclidine-3-carboxylate with hydrogen using Raney nickel.

In the first step of the process, quinuclidine-3-one hydrochloride is reacted with sodium cyanide in a known manner in an aqueous solution at 2° to 25° C. The cooling is necessary because at a higher temperature, the resulting cyanohydrin could reversibly decompose to its educts again. After a reaction period of 1 to 5 hours, 3-cyano-3-hydroxy-quinuclidine-3 is obtained in a yield of 95% by the following reaction.

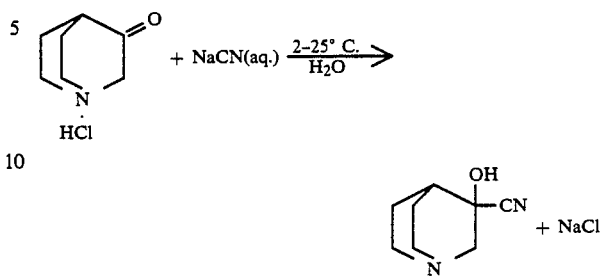

In the next step, the carefully dried 3-cyano-3-hydroxy-quinuclidine (H₂O content under 0.1%) is dissolved in methanol and transformed into the iminoether derivative by introduction of hydrogen chloride gas by the following reaction.

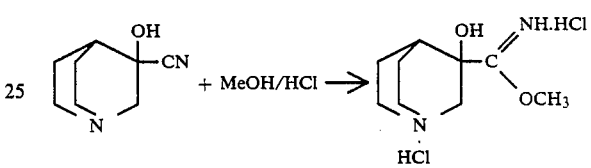

In the presence of traces of water, the undesired free acid would form. After complete formation of the iminoether intermediate, water and then alkali are added for the release of the ester to obtain methyl 3-hydroxy-quinuclidine-carboxylate in a yield of 68%.

By this change in process as compared with the prior art, a most major improvement becomes possible. Apart from the good yield, the period of 96 hours required by the process described in the prior art is reduced to 15 to 24 hours with an equal yield. The reaction proceeds as follows.

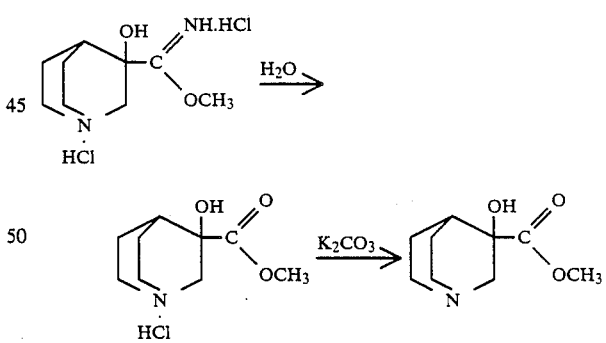

The removal of the hydroxy group is effected with excess refluxing thionyl chloride by the following reaction

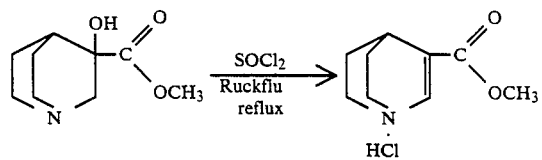

This is surprising inasmuch as in the reaction of this alcohol with thionyl chloride, no chlorine compound is formed that is, not a substitution but elimination of the hydroxy takes place.

Another surprising fact is that this reaction is possible only with the methyl ester and not with the ethyl ester which can be produced more easily and with a better yield. After the reaction, excessive thionyl chloride is distilled off and reused in the next batch and the yield in this reaction is 76%.

The double bond produced by dehydration is eliminated in the next step by addition of hydrogen and is transformed into a single bond by the following reaction.

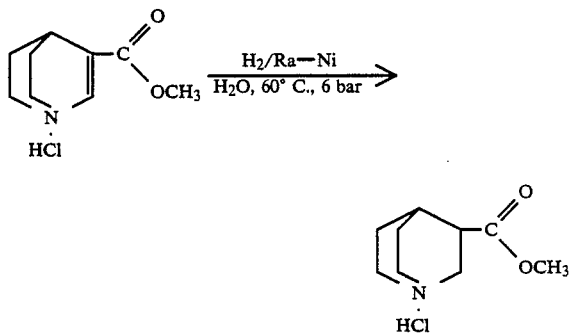

In this step, the yield is improved further as the literature describes the hydrogenation to the methyl quinuclidine-3-carboxylate hydrochloride with platinum oxide in alcohol with a yield of 9.5%. It succeeds, surprisingly, with the much cheaper Raney nickel in water. Because of the possible hydrolysis and arrangement of the ester, the reaction conditions must be comparatively mild, i.e., 1 to 15 bars at temperatures in the range of 20° to 100° C. Thus, for example, at 60° C. and 6 bars, the reaction is completed after 4 hours and the yield practically quantitative. This result is surprising because of the considerable steric hindrance at the double bond, and especially since with noble metal catalysts such as platinum, palladium or rhodium, some of which are more active, no reaction took place and instead, the educt was isolated.

For the last reaction step, the ester reduction, the quinuclidine ester is alkalinized, the quinuclidine ester base is extracted with toluene, freed from water, and, in a known manner is reduced e.g. with lithium aluminum hydride.

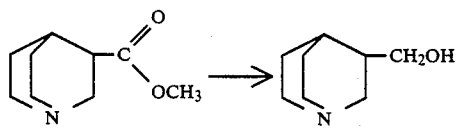

In this reaction, the yield of quinuclidine-3-methanol is 60%. Hence, over all, the total yield is about 30%.

In the following examples there are described in several preferred embodiments to illustrate the invention. However, it should be understood that the invention is not intended to be limited to the specific embodiments.

EXAMPLE 1

3-cyano-3-hydroxy-quinuclidine 1,420 g (8.78 mole) of quinuclidine-3-one-hydrochloride were dissolved in 1800 ml of cold water and at 15° C., 432 g (8.81 mole) of sodium cyanide and 1600 of ml water were added dropwise over one hour followed by stirring for another hour at this temperature. The mixture was filtered, washed with cold water, and dried at 60° C. to obtain 1,290 g (8.48 mole) of 3-cyano-3-hydroxy-quinuclidine (97% yield), in the form of white crystals having a melting point of 157° to 159° C.

EXAMPLE 2

Methyl 3-hydroxy-quinuclidin-3-carboxylate 2,780 ml of methanol were mixed with 890 g (5.85 mole) of 3-cyano-3-hydroxy-quinuclidine of Example 1 and at 25° to 30° C., 1,440 g of hydrogen chloride gas was slowly introduced until saturation was reached. The mixture was refluxed for 16 hours and then methanol was distilled off under vacuum. The residue was added to 2,000 ml of water and then alkalinized with 1200 ml of concentrated potassium carbonate solution (pH 11–12) After stirring with 1,400 ml of chloroform, the phases were separated and the organic phase was dried and chloroform was removed by distillation to obtain 740 g (4.0 moles) of methyl 3-hydroxy-quinuclidine-3-carboxylate (68% yield) with a melting point of 119° to 122° C.

EXAMPLE 3

Methyl 1-azabicyclo(2,2,2)oct-2-ene-3-carboxylate 1,180 g of thionyl chloride were sufficiently cooled so that upon portionwise addition of 150 g (0.81 mole) of methyl 3-hydroxy-quinuclidine-3-carboxylate of Example 2, a temperature of 15° C. was not exceeded. Then, the mixture was refluxed for 15 hours and subsequently excess thionyl chloride was distilled off. The residue was admixed at elevated temperature with 350 ml of isopropanol, again heating at reflux. After cooling to room temperature, the suspension was filtered and the residue was washed with 80 ml of isopropanol and dried to obtain 123 g (0.61 mole) of methyl 1-azabicyclo(2,2,-2)oct-2-ene-3-carboxylate hydrochloride (75% yield) having a melting point of 175° to 177° C.

EXAMPLE 4

Methyl 1-azabicyclo(2,2,2)octane-3-carboxylae hydrochloride 500 g (2.45 mole) of methyl 1-azabicyclo(2,2,2)oct-2-ene-3-carboxylate hydrochloride of Example 3 were dissolved in 1,250 ml of water and the solution was placed in an autoclave. After addition of 70 g of Raney nickel, the autoclave was heated to 60° C. and by introducing hydrogen, a pressure of 6 bars was adjusted. After 6 hours and absorption of 7 g (3.5 mole) of hydrogen gas, the reaction was stopped and the catalyst was filtered off. The water was distilled off under vacuum and the residue was dried in an desiccator to obtain 500 g (2.43 mole) of methyl quinuclidiene-3-carboxylate hydrochloride (99% of theory) as white hygroscopic needles having a melting point of 161° to 164° C. After crystalliation from acetone, the melting point rose to 168° to 169° C.

EXAMPLE 5

Quinuclidine-3-methanol 90 g (2.37 mole) of lithium aluminum hydride in 200 ml of diethyl ether were slowly added with stirring to a solution of 231 g (1.37 mole) of methyl quinuclidine-3-carboxylate of Example 4 in 1,000 ml of diethyl ether. Reflux was continued for 3 hours and the excess lithium alanate was carefully decomposed with 500 ml of water with proper cooling. The reaction mixture was filtered and after separation of the phases, the ether phase was dried over magnesium sulfate. Thereafter, the ether was distilled off to obtain 116 g (0.82 mole) of quinuclidine-3-methanol (60% yield) as a colorless oil.

Various modifications of the process of the invention may be made without departing from the spirit or scope thereof and it should be understood that the invention is intended to be limited only as defined in the appended claims.

What we claim is:

1. A process for the preparation of quinuclidine-3-methanol comprising reacting quinuclidine-3-one acid addition salt with an alkali metal cyanide in an aqueous media to obtain 3-cyano-3-hydroxy-quinuclidine, reacting the latter with anhydrous methanol in the presence of hydrogen chloride gas followed by treatment with aqueous alkali to obtain methyl 3-hydroxy-quinuclidine-3-carboxylate, reacting the latter with thionyl chloride to form methyl 1-azabicyclo(2,2,2)oct-2-ene-3-carboxylate, hydrogenating the latter with Raney nickel to obtain methyl 1-azabicyclo(2,2,2)octane-3-carboxylate and reducing the latter to obtain quinuclidine-3-methanol.

* * * * *